United States Patent [19]
Intille et al.

[11] 3,966,798
[45] June 29, 1976

[54] CATALYTIC COUPLING OF ALLYLIC COMPOUNDS TO SUBSTITUTED OLEFINS

[75] Inventors: George M. Intille; Gary R. Beck, both of St. Louis, Mo.

[73] Assignee: Monsanto Company, St. Louis, Mo.

[22] Filed: Dec. 4, 1974

[21] Appl. No.: 529,674

[52] U.S. Cl. .......................... 260/486 R; 260/343.5; 260/465.9; 260/476 R; 260/533 A; 260/561 N; 260/614 R
[51] Int. Cl.$^2$ ......................................... C07C 69/52
[58] Field of Search .............................. 260/486 R

[56] References Cited
UNITED STATES PATENTS

| | | | |
|---|---|---|---|
| 3,113,149 | 12/1963 | Probst et al. ................... | 260/486 R |
| 3,586,714 | 6/1971 | Dubini et al. ................... | 260/486 R |
| 3,783,136 | 1/1974 | Inukai et al. ................... | 260/486 |

*Primary Examiner*—Paul J. Killos

[57] ABSTRACT

Allylic compounds are carbon-to-carbon coupled to substituted olefins by contacting the two compounds in the presence of a catalyst system comprising a Group VIII metal component, a bromine or iodine component, and a Group VA component. The foregoing catalytic process also promotes the intramolecular, carbon-carbon coupling of allylic and substituted olefin groups wherein both processes provide a method for producing sorbates and related compounds.

19 Claims, No Drawings

CATALYTIC COUPLING OF ALLYLIC COMPOUNDS TO SUBSTITUTED OLEFINS

BACKGROUND OF THE INVENTION

The invention pertains to a catalytic process for coupling allylic compounds and substituted olefins. In another aspect this invention relates to a catalytic process for intra-molecular, carbon-carbon coupling of allylic and substituted olefinic groups which are present in the same compound. Yet in another aspect this invention relates to a catalyst system for coupling allylic and substituted olefinic groups wherein the catalyst system is comprised of a Group VIII metal component, a bromine or iodine component, and a Group V A component. In still another aspect this invention relates to a catalytic process for preparing sorbates and related compounds.

The present method for producing sorbic acid and related compounds involves the reaction of ketene and crotynaldehyde which results in an intractable polymer which must be acid hydrolyzed. The hydrolysis of the polymer results in a mixture of products requiring repeated and difficult separation and purification procedures.

The preparation of sorbates and related compounds because of their multiple functionality, can also involve numerous and cumbersome process steps employing exotic starting materials. For example, the art has recently reported that allyl bromide, tributyl amine can be reacted with methyl acrylate to form methyl sorbate and tributyl ammonium bromide in the presence of palladium acetate and triphenyl phosphine however the use of a stoichiometric amount of the bromide reduces the attractiveness of the process. The elimination of the requirement of stoichiometric bromide in sorbate production would represent an important advancement over the art.

Prior to the catalytic process of this invention, coupling of allylic compounds and substitued olefins required the inventive catalytic process, the art is presented with a more feasible route to doubly unsaturated, substituted hydrocarbons using available and inexpensive starting materials. For example, a route to sorbic acid and its derivatives from allyl alcohol and methyl acrylate is provided by the use of the catalyst system comprising a Group VIII component, a halogen component, and a Group V A component. The inventive reaction of allylic compounds with substituted olefinic compounds allows both the metal components of the catalyst system and the halogen components to be present in substantially less than stoichiometric amounts.

SUMMARY OF THE INVENTION

In accordance with the present invention a feed comprising substituted allylic compounds are contacted with substituted, olefinically unsaturated compounds to yield corresponding alkadienyl compounds or derivatives thereof, by contacting the feedstock at a temperature of from about 25°C to about 300°C in the presence of a catalyst system comprising a Group VIII metal component, a bromine or iodine component, and a Group V A component. The two feedstock reactants are in fluid form, either gaseous or liquid depending on the compounds, temperature and pressure. The inventive process is particularly advantageous due to the availability of suitable allylic compounds and the utilization of substantially less than stoichiometric amounts of the catalyst system which in turn promotes simplified separation procedures for the reaction product.

One application of the above-described invention is the production of methyl sorbate from allyl alcohol and methyl acrylate. Sorbic acid and its derivatives, for example, the potassium salt, can be prepared from methyl sorbate through known processes such as acid as base hydrolysis. In addition, it is possible by methods described herein to form derivatives of sorbic acid such as methyl sorbate or sorbolactone, hydroxyor alkoxyhexenoic acids, esters of these or sorbic acids or other desireable derivatives such as the potassium salt and the like.

DESCRIPTION OF THE PREFERRED EMBODIMENTS

According to the present invention, the catalyst system comprises a Group VIII component, bromine or iodine component and a Group V A component with the Group VIII component generally present in the form of a coordination compound of a Group VIII metal. The bromine or iodine and Group V A compound as well as possibly the olefin and allyl groups provide the ligands for such coordination compounds. The various catalyst system components can be provided by introducing into the reaction zone, a coordination compound containing the halogen and Group V A component or in the alternative the components may be provided by introducing them separately into the reaction zone. Furthermore a Group VIII olefin or Group VIII allyl compound may be employed as source of the Group VIII component. Various other ligands may be utilized if desired.

The Group VIII component of the catalyst system can be chosen from the elements contained in the Group VIII of the standard periodic table of elements a found in the Handbook of Chemistry and Physics, including, Pd, Ni, Pt, Rh, Ir, Os, and Ru, with Pd being the preferred Group VIII metal. Among the materials which may be charged to the reaction zone to provide the Group VIII component of the present invention are Group VIII metals such as palladium, platinum, nickel, Group VIII metal salts, oxides, organo compounds, coordination compounds and the like. Specific examples of materials capable of providing the Group VIII constituent of the catalyst system of the present invention may be taken from the following non- limiting partial list of suitable materials such as:

| | | |
|---|---|---|
| Pd | Ni | [Rh(CO)$_2$I$_4$]$^-$ |
| PdO | NiO | |
| PdCl$_2$ | NiBr$_2$ | Ir |
| PdBr$_2$ | allyl$_2$Ni | Ir$_2$O$_3$ |
| PdI$_2$ | Ni(CO)$_4$ | IrCl(CO)(P$\phi_3$)$_2$ |
| Na$_2$PdCl$_4$ | Ni(P$\phi_3$)$_4$ | |
| H$_2$PdBr$_4$ | HRhCl(P$\phi_3$)$_2$ | Os |
| Pd(CO)$_2$Cl$_2$ | | Os$_3$(CO)$_{12}$ |
| (allyl PdCl)$_2$ | Pt | Os$_3$(CO)$_9$(P$\phi_3$)$_3$ |
| allyl$_2$ Pd | PtO | |
| allyl Pd(Cl)PO$_3$ | PtCl$_2$ | RuCl$_3$ |
| (NO)$_2$ Pd I$_4$ | PtI$_4$ | Ru(CO)$_5$ |
| PdCl$_2$(P$\phi_3$)$_2$ | K$_2$PtI$_6$ | |
| Pd(P$\phi_3$)$_4$ | H$_2$PtBr$_6$ | |
| Pd(P$\phi_3$)$_2$ | Pt(P$\phi_3$)$_4$ | |
| HPdCl(P$\phi_3$)$_2$ | | |
| Pd($\phi$Ac)$_2$ | Rh | |
| (NH$_4$)$_2$PdBr$_4$ | Rh$_6$(CO)$_{16}$ | |
| Pd(acac)$_2$ | HRh(CO)$_2$(P$\phi_3$)$_2$ | | and the like.

Since the above materials are capable of providing the Group VIII component but may or may not include the halogen component, it may be necessary to introduce the halogen component separately into the reaction zone. For example, if a palladium component is introduced as palladium acetate it will be necessary to introduce a halogen component such as allyl iodide, tetraethyl ammonium bromide, hydrogen bromide, bromine gas, and the like into the reaction zone. The halogen component for the purposes of this invention is bromine or iodine and may be present in varying amounts, however it is generally preferred that it be present in at least equimolar amounts to that of the Group VIII metal. The Group VIII metal to halogen equimolar ratio may range from about 1:1 to about 1:1000 although ratios of from about 1:1 to about 1:100 are preferred. The present invention is most useful when it is desireable to use ratios of from about 1:1 to about 1:10. The halogen component may be supplied in combination with a Group VIII metal component or added separately or as a combination of both. If it is desired to charge all or part of the hydrogen component separately, suitable halogen containing components may be supplied from the following list of halogen or halogen containing compounds such as

R—X where R is hydrogen or a hydrocarbon having from 1 to about 30 carbon atoms per molecule and can be selected from groups such as alkyl, alkenyl, alkynyl, acyl, allyl and mixtures thereof, and X is a halogen such as bromine or iodine;

$X_2$ or $X_3$ where X is bromine or iodine;

where R and X are defined as hereinabove;

$M_y X_z$ where M is any metal, X is bromine or iodine, y and z are integers of one or more; and $ER_4X_3$ or $ER_3 X_2$ where R and X are defined hereinabove and E is a Group V A element.

The halogen employed is either bromine or iodine, with bromine being the most preferred.

The Group V A component of the catalyst system may also be supplied separately or as part of the palladium or halogen component. When it is desired to supply all or part of the Group V A components separately it may be supplied from the following non-limiting compounds:

$ER_3$ where R is hydrogen or a hydrocarbon having from 1 to about 30 carbon atoms per molecule and may be selected from groups such as alkyl, alkenyl, alkynyl, aryl, allyl and mixtures thereof, and E is a Group V A element; and $ER_4 X, ER_3 X_2$; or $R_2E—R'—ER_2$ where E and R are defined as above and X is bromine, or iodine, and R' is is a divalent hydrocarbyl group.

The amount of Group V A component can also vary. The ratio of the Group VIII component to Group V component may range from 1:1 to about 1:1000 with the preferred range being from 1:1 to about 1:100, and 1:1 to about 1:10 being most preferred.

Under liquid phase conditions the reaction medium employed may be comprised of just the feedstock allylic compound and substituted olefin and mixtures thereof or may include any solvent compatible with the catalyst and reaction system. Solvents which are suitable include paraffinic hydrocarbons from 4–50 carbon atoms, aromatic hydrocarbons from 6-40 carbon atoms, alcohols, ethers, esters, ketones, nitriles, aromatic amines and chlorinated paraffins or aromatics. The following list exemplifies such solvents: dodecane, hexadecane, naphthalene, biphenyl methyl propionate, dimethyl phthalate, isopropyl ether, acetone, benzonitrile, pyridine, chlorinated biphenyl ethanol, and the like.

Suitable allylic components according to the invention can be selected from compounds having the general formula:

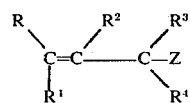

where R, $R^1$, $R^2$, $R^3$, and $R^4$ are each independently hydrogen or hydrocarbyl radicals having from 1 to about 20 carbon atoms per molecule, and Z is hydrogen, chlorine, hydroxyl, ether, or ester groups. Examples of suitable allylic compounds according to the invention include allyl alcohol, allyl acrylate, allyl ether, propylene and the like.

The particular advantage of the present invention is when Z is defined as above and the reaction can be performed in the presence of only a catalytic amount of bromine and/or iodine as part of the catalyst system.

For the purpose of describing this invention, suitable substituted olefinic components will be defined as compounds having the general formula

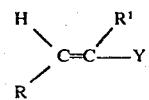

where R and $R^1$ are each independently hydrogen or hydrocarbyl radicals having from 1 to about 20 carbon atoms per molecule, and Y is selected from one of the following radicals:

and the like where R is a hydrocarbyl radical. Examples of suitable, substituted olefinic compounds according to the above formula include methyl acrylate, methyl methacrylate, acrylic acid, crotonic acid, acrylamide, acrolein, 3 pentene-zone, acrylonitrile, and the like.

The allylic and olefinic components can be supplied in the form of a compound containing both functional groups in one molecule such as allyl acrylate

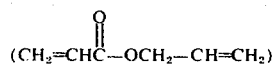

or methallyl methacrylate. The reaction of these compounds according to the inventive process forms doubly unsaturated substituted compounds in which a new intramolecular carbon-carbon bond is formed between the allylic group and the olefin group. The resulting product has the general formula

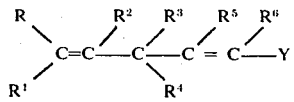 (1)

where R, R$^1$, R$^2$, R$^3$, R$^4$, and R$^6$ are each independently hydrogen or any hydrocarbyl radical and Y is selected from one of the following radicals -C-(OR)$_2$,

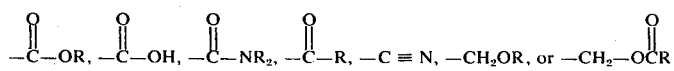

and the like, where R is a hydrocarbyl radical.

Under reaction conditions of the invention, double bond iomerization may also occur thus resulting in compounds of the formula:

$$R_3C-CR=CR-CR=CR-Y \quad (2)$$

where the R's may be the same or different and as Y, are defined as above. Also sorbates and derivatives such as those arising from hydration of one of the double bonds may be formed resulting in compounds of the formula:

 (3)

or related isomers or derivatives where R and Y are defined as above, and Y' is a hydroxy, alkoxy, or carboxylate groups. The compounds as presented by formulae (1) through (3) above and formula (4) below are produced according to the inventive process. The components of formulae (1) and (2) are comprised of a pentadienyl radical having one of the following formulae:

$$R_7 [ C = C - C - C = C - Y ] \quad (a)$$
$$R_7 [ C - C = C - C = C - Y ] \quad (b)$$
$$R_7 [ C = C - C = C - C - Y ] \quad (c)$$

where Y is

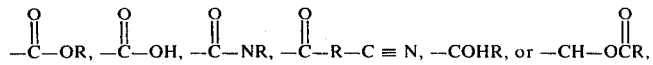

and R is at least one of hydrogen, or a hydrocarbyl radical having from 1 to about 20 carbon atoms per molecule. The compounds of formula (3) represent a derivative of formula (a) wherein one of the double bonds of the pentadienyl radical has been reduced and replaced by a Y'. All three radicals as represented for formulae (a) (b) and (c) produce similar derivatives upon hydration of either of the double bonds according to the invention.

In the above compounds formulae (1) through (3) and (a) through (c) where Y is a COOH group, cyclization may occur to form lactones and other carbon-carbon coupled compounds such as:

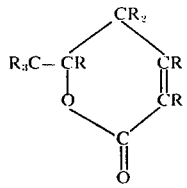 (4)

and the like.

Examples of compounds produced according to the invention include sorbic acid methyl 2,5-hexadienoate, 5 methyl hexadienenitrile and derivatives such as sorbalactone, hydroxy hexenoic acid allyl (allyloxy hexenoate) and the like.

In accordance with the present invention the reaction of the allylic component and olefin component may be carried out by intimately contacting the above defined feed components which depending on the number of carbon atom number per molecule and operating conditions may be in the vapor or liquid phase. For example as a liquid phase containing a catalyst system such as allyl palladium chloride dimer, a halogen containing promoting component such a tetraethyl ammonium bromide, and a Group V component such a triphenyl phosphine, the coupling reaction proceeds under conditions of temperature and pressure as described herein to form the double unsaturated product. The particular conditions selected are about the same whether the feed components are charged as a vapor or liquid. The temperature will accordingly be in the range of 25°C to 300°C with the preferred range being 80°C to 150°C.

Alternatively the reaction may be conducted through the reaction of the feed components over the catalyst system described above which are dispersed upon an inert support. Such a catalyst system may be operated as a conventional fixed bed reactor. For example methyl acrylate and allyl alcohol may be passed over a catalyst system such as Pd(P$\phi_3$)$_2$(H)Br dispersed on an inert support material such as alundum, activated carbon, clays, alumina, silica-alumina, ceramics, and the like in a fixed bed reactor to produce methyl sorbate. However the use of a liquid reaction medium as described is preferred in the process of this invention.

While any relative amount of the two feedstocks may be used, the stoichiometry of the reaction requires one mole of allylic compound per mole of olefin compound. Therefore while the ratio may vary from 1:1000 to 1000:1 ratios of about 1:1 are preferred.

The reaction rate is dependent in part on catalyst concentration and temperature. Concentration of the palladium component of the catalyst system in the liquid phase between 1×10$^{-6}$ moles/liter to 1 mole/liter are normally employed with the preferred range being 1×10$^{-4}$ to 1×10$^{-1}$ moles/liter and concentrations near 1×10$^{-2}$ moles/liter being most preferred. However higher concentration may be used if desired. The concentration of the halogen component and Group V A component are fixed by the respective ratios to palladium.

In carrying out the reaction of allylic compounds with substituted olefins the product purification can be performed by distillation to remove the products while the remaining lower boiling components which contain the components of the catalyst system can be recycled. Alternatively, other methods of purification such as extraction or precipitation may be suitable.

In order to provide for a better understanding of the process of the present invention as described, a number of specific embodiments of the process are presented below. These examples presented below are not to be construed in any manner as limiting to the scope of the invention.

EXAMPLE I

A quantity of 1.1 grams palladium acetate, 0.61 cc-47° by weight hydrogen bromide, 5.25 grams triphenyl phosphine, 45 cc allyl alcohol, and 60 cc methyl acrylate is introduced into a reaction chamber and heated to 120°C for a period of 15 hours. Methyl sorbate is produced to the extent of 15% by weight of the final reaction solution.

EXAMPLE II

Quantities of 1.9 grams alyl allyl chloride dimer, 2.75 grams tetraethyl ammonium bromide, 5.25 grams of triphenyl phosphine, 45 cc allyl alcohol, and 60 cc methyl acrylate are introduced into a reaction chamber and heated to 120°C for 20 hours. Methyl sorbate is produced to the extent of 10% by weight of the final reaction solution.

EXAMPLE III

Quantities of 5 millimoles palladium acetate, 20 millimoles triphenyl phosphine, 5 millimoles of hydrogen bromide, 600 millimoles allyl alcohol, and 600 millimoles methyl acrylate are introduced into a reaction chamber and heated to 135°C for 20 hours. The final reaction solution produced 15% by weight methyl sorbate, allyl sorbate, and traces of methyl cinnamate.

EXAMPLE IV

The procedure of Example 3 is repeated in the presence of 100 milliliters of benzonitrile solvent. The final reaction solution contains approximately the same relative amounts of methyl sorbate, allyl sorbate, and methyl cinnamate.

EXAMPLE V

Quantities of 100 cc methyl acrylate, 1.9 grams palladium bromide, 2.5 grams tetraethyl ammonium bromide, and 5.25 grams triphenyl phosphine is introduced into a 300 cc autoclave under the pressure provided by 15 grams of propylene and heated to 190°C for 20 hours. The final reaction solution contained a trace of methyl sorbate.

EXAMPLE VI

A quantity of 100 grams allyl acrylate is introduced into a reaction chamber in the presence of a catalytic amount, i.e. 1 gram of palladium acetate, equal molar amount of hydrogen bromide to that of the palladium acetate, and a 2 molar amount of triphenylphosphine to that of the palladium acetate; and heated to 120°C for 20 hours. The final reaction solution produces sorbolactone which upon hydrolysis results in 3 grams or sorbic acid.

EXAMPLE VII

Quantities of 100 grams of equal molar amounts of allyl alcohol and methyl acrylate, 1 gram of palladium acetate, equal molar amounts of tetraethyl ammonium bromide based on palladium acetate, and a 2 molar amount of triphenyl phosphine based on palladium acetate are introduced to a reaction chamber and heated to 185°C for 20 hours. The resulting reaction solution produces, as determined by GCA, methyl sorbate, metyl (alkyloxy hexeneoate), allyl (allyloxy hexenoate) and methyl cinnamate.

The following Example VIII and IX are not according to the invention and are presented for the purpose of demonstrating the use of a stoichiometric quantity of bromide in the form of alkyl bromide; and the inoperability of the process, absent any bromide or iodide either in a catalytic amount or as a reactive compound.

EXAMPLE VIII

Quantities of 1.1 grams palladium acetate, 5.25 grams triphenyl phosphine, 42 cc alkyl bromide, 45 cc methyl acrylate and 119 cc tributyl amine are introduced into a reactor chamber and heated to 120°C for 27 hours. The resulting reaction mass is extracted with ether followed by distillation yielding 2.9 grams (4% yield) of methyl sorbate and alkyl-tributyl ammonium bromide as the major product.

EXAMPLE IX

Quantities of 1.1 grams palladium acetate, 5.25 grams triphenyl phosphine, 45 cc allyl alcohol, 60 cc methyl acrylate are introduced into a reaction chamber and heated to 120°C for 72 hours. Methyl sorbate is not found to be present by GC analysis methods.

What is claimed is:
1. A catalytic process for carbon to carbon coupling of allylic compounds with substituted olefins, comprising:

contacting allylic compounds having the formula

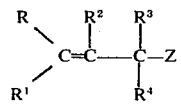

where $R$, $R^1$, $R^2$, $R^3$, and $R^4$ are each independently hydrogen, or a hydrocarbyl radical, and Z is hydrogen, chlorine, an alcohol, or —OR group with R having a hydrocarbyl radical; and substituted olefins having the formula

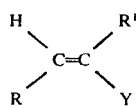

where R and $R^1$ are each independently hydrogen or a hydrocarbyl radical and Y is one of

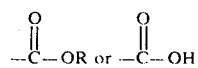

with R being a hydrocarbyl radical;

said contacting occurring in the presence of a catalyst system comprised of a a Group VIII metal component, at least one of a bromine or iodine component, and Group VA component.

2. A process according to claim 1 wherein the allylic compound is allyl alcohol.

3. A process according to claim 1 wherein the allylic compound is propylene.

4. A process according to claim 1 wherein the allylic compound is allyl acetate.

5. A process according to claim 1 wherein the substituted olefin is methyl acrylate.

6. A process according to claim 1 wherein the substituted olefin is acrylic acid.

7. A process according to claim 1 wherein the Group VIII metal component is palladium 8. A process according to claim 1 wherein the Group VA component is phosphine.

9. A catalytic process for intramolecular, carbon-to-carbon coupling of allylic and substituted olefin groups wherein both groups are contained in the same compound comprising:

contacting the compound with a catalyst system comprised of a Group VIII metal component, at least one of a bromine or iodine component, and a Group V A component.

10. A process according to claim 9 wherein the compound is allyl acrylate.

11. A process according to claim 9 wherein the compound is methallyl methacrylate.

12. A process according to claim 9 wherein the Group VIII metal component is palladium.

13. A process according to claim 9 wherein the Group V A component is phosphine.

14. A catalytic process for producing compounds having a pentadienyl radical selected from the group consisting of:

(a) $R_7[C=C-C-C=C-Y]$
(b) $R_7[C-C=C-C=C-Y]$
(c) $R_7[C=C-C=C-C-Y]$ where Y is

and R is at least one of hydrogen, or an alkyl or alkenyl radical having from 1 to about 20 carbon atoms per molecule: comprising contacting allylic compounds with substituted olefins in the presence of a catalyst system comprised of a Group VIII metal component, at least one of bromine or iodine component, and a Group V A component.

15. A process according to claim 13 wherein the allylic compound has the formula:

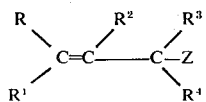

where R, $R^1$, $R^2$, $R^3$, and $R^4$ are each independently hydrogen, or a hydrocarbyl radical; and Z is hydrogen, chlorine, an alcohol, -OR, or

group, with R being a hydrocarbyl radical.

16. A process according to claim 13 wherein the substituted olefins have the formula:

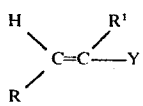

where R and $R^1$ are each independently hydrogen or a hydrocarbyl radical and Y is selected from the group consisting of

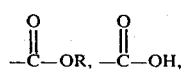

with R being a hydrocarbyl radical.

17. A process according to claim 13 wherein compounds having both allylic and substituted olefin groups in the same molecule are contacted with the catalyst system.

18. A process according to claim 13 wherein the pentadienyl radical has one double bond reduced to a single bond and is substituted with a hydroxy, alkoxy or carboxylate group.

19. A process according to claim 18 wherein Y is a carboxylate and the substitution is a carboxylate resulting in cyclic, carbon-to-carbon bonding of the pentadienyl radical.

* * * * *

UNITED STATES PATENT OFFICE
CERTIFICATE OF CORRECTION

PATENT NO. : 3,966,798
DATED : June 29, 1976
INVENTOR(S) : G. M. Intille et al

It is certified that error appears in the above–identified patent and that said Letters Patent are hereby corrected as shown below:

Column 7, Example 2, first line, should read,

--Quantities of 1.9 grams allyl palladium chloride dimer, 2.75...--

Signed and Sealed this

First Day of March 1977

[SEAL]

Attest:

RUTH C. MASON
Attesting Officer

C. MARSHALL DANN
Commissioner of Patents and Trademarks